(12) United States Patent
Ranchod et al.

(10) Patent No.: US 10,736,506 B2
(45) Date of Patent: Aug. 11, 2020

(54) COMPOSITE IMAGE WITH CROSS-CHANNEL ILLUMINATION

(71) Applicant: BROADSPOT IMAGING CORP., Richmond, CA (US)

(72) Inventors: Tushar M. Ranchod, Berkeley, CA (US); Brendan Hamel-Bissell, San Francisco, CA (US); Benjamin A. Jacobson, Santa Barbara, CA (US); Andre E. Adams, Tiburon, CA (US); Clark Pentico, Simi Valley, CA (US)

(73) Assignee: BROADSPOT IMAGING CORP, Emeryville, CA (US)

( * ) Notice: Subject to any disclaimer, the term of this patent is extended or adjusted under 35 U.S.C. 154(b) by 0 days.

(21) Appl. No.: 16/430,120

(22) Filed: Jun. 3, 2019

(65) Prior Publication Data
US 2019/0380576 A1    Dec. 19, 2019

Related U.S. Application Data

(60) Provisional application No. 62/685,082, filed on Jun. 14, 2018.

(51) Int. Cl.
*A61B 3/14*   (2006.01)
*A61B 3/00*   (2006.01)
*A61B 3/12*   (2006.01)

(52) U.S. Cl.
CPC ............ *A61B 3/145* (2013.01); *A61B 3/0008* (2013.01); *A61B 3/12* (2013.01)

(58) Field of Classification Search
CPC ........... A61B 3/14; A61B 3/0025; A61B 3/12; A61B 3/102; A61B 3/0008
USPC ......................................................... 351/206
See application file for complete search history.

(56) References Cited

U.S. PATENT DOCUMENTS

| 2007/0132953 A1 | 6/2007 | Silverstein |
| 2011/0228142 A1 | 9/2011 | Brueckner et al. |
| 2012/0162605 A1 | 6/2012 | Koest |

(Continued)

OTHER PUBLICATIONS

International Search Report dated Aug. 19, 2019 as received in Application No. PCT/US2019/035527.

(Continued)

*Primary Examiner* — Mohammed A Hasan
(74) *Attorney, Agent, or Firm* — Maschoff Brennan (57) ABSTRACT

An imaging device may include first and second optical channels, where each of the first and second optical channels include a discrete optical imaging pathway. The first and second optical channels may be aimed at different angles relative to each other, and each may be directed towards corresponding partially overlapping zones of an object for imaging. Each of the optical channels may include an illuminating source configured to be turned on or off, where illumination from the illuminating sources follow respective illumination paths to the object. Each of the optical channels may additionally include lenses shared by both the respective optical imaging pathways and the respective illumination paths, and each may include an image sensor. The imaging device may also include a computing device configured to turn on the illuminating source of the first optical channel while capturing an image using the image sensor of the second optical channel.

19 Claims, 9 Drawing Sheets

(56) References Cited

U.S. PATENT DOCUMENTS

2013/0271728 A1* 10/2013 Ranchod ................. A61B 3/14
                                                              351/206
2015/0334374 A1    11/2015  Yun et al.
2017/0332065 A1    11/2017  Regensburger et al.

OTHER PUBLICATIONS

Written Opinion of the International Searching Authority dated Aug. 19, 2019 as received in Application No. PCT/US2019/035527.

* cited by examiner

COMPOSITE IMAGE WITH CROSS-CHANNEL ILLUMINATION

CROSS-REFERENCE TO RELATED APPLICATION

This application claims priority to U.S. Provisional Patent Application No. 62/685,082, filed on Jun. 14, 2018, the disclosure of which is incorporated herein by reference in its entirety.

FIELD

The application relates generally to devices and systems used in generating a composite image with cross-channel illumination.

BACKGROUND

Ocular imaging is commonly used both to screen for diseases and to document findings discovered during clinical examination of the eye. Specifically, documentation and analysis of retinal imaging may be relevant to comprehensive eye examinations and full evaluations of current conditions, treatment, and/or early prevention of various eye conditions and diseases.

The subject matter claimed herein is not limited to embodiments that solve any disadvantages or that operate only in environments such as those described above. Rather, this background is only provided to illustrate one example technology area where some embodiments described herein may be practiced.

SUMMARY

Embodiments of the disclosure include an imaging device that includes a first and a second optical channel. Each optical channel of the first and second optical channels may include a discrete optical imaging pathway, where the optical imaging pathways of the first and second optical channels may be aimed at different angles relative to each other, and each may be directed towards corresponding partially overlapping zones of an object. Each of the optical channels may additionally include an illuminating source that is configured to be turned on or off, where illumination from the illuminating source may follow an illumination path to the object. Each of the optical channels may also include one or more lenses shared by both the discrete optical imaging pathway and the illumination path, and an image sensor. The imaging device may also include a computing device configured to turn on the illuminating source of the first optical channel while capturing an image using the image sensor of the second optical channel.

Any of the imaging devices of the present disclosure may be configured such that the first and the second optical channels are aimed at equal angles relative to a central axis between the first and the second optical channels, the central axis pointing towards the object.

Any of the imaging devices of the present disclosure may be configured such that the first and the second optical channels are aimed such that the discrete optical imaging pathways and the illumination pathways of both the first and the second optical channels pass through a pupil of an eye to image a retina of the eye.

Any of the imaging devices of the present disclosure may further configured the computing device to alternate between (i) turning off the illuminating source of the second optical channel, and turning on the illuminating source of the first optical channel so the illuminating source of the first optical channel is on while capturing a first image using the image sensor of the second optical channel, and (ii) turning off the illuminating source of the first optical channel, and turning on the illuminating source of the second optical channel so the illuminating source of the second optical channel is on while capturing a second image using the image sensor of the first optical channel.

Any of the imaging devices of the present disclosure may be configured such that the first and the second images are combined to form a real time video of the object.

Any of the imaging devices of the present disclosure may be configured such that at least one of the first image and the second image are stretched or skewed such that the first image and the second image appear to have been captured from a common perspective.

Any of the imaging devices of the present disclosure may be configured such that a given region of the first image that includes an artifact is replaced with a corresponding region of the second image, the corresponding region of the second image showing the given region without the artifact.

Any of the imaging devices of the present disclosure may be configured such that the illuminating source is offset from the image sensor.

Any of the imaging devices of the present disclosure may be configured such that the illuminating source is offset axially from the image sensor within a same enclosure as the image sensor.

Any of the imaging devices of the present disclosure may be configured such that the first optical channel further includes a beam splitter, and where the illuminating source is in a branch of the first optical channel, and where the beam splitter is at an intersection of the branch of the first optical channel, the beam splitter directing illumination rays towards the object.

Any of the imaging devices of the present disclosure may further comprise a third optical channel, where the third optical channel includes a third image sensor, a third optical imaging pathway from the third image sensor to the object, and a third illuminating source configured to be turned on or off, where illumination from the third illuminating source follows a third illumination path to the object.

Any of the imaging devices of the present disclosure may be configured such that the computing device is configured to instruct the illuminating sources of the first and the second optical channels to be turned on while an image is captured using the third image sensor of the third optical channel.

Any of the imaging devices of the present disclosure may be configured such that the computing device is configured to instruct the third illuminating source to be turned on while images are captured by the image sensors of the first and the second optical channels.

Any of the imaging devices of the present disclosure may be configured such that the first optical channel further includes a second illuminating source, the second illuminating source following a second illumination pathway and having different properties from the illuminating source of the first optical channel.

Any of the imaging devices of the present disclosure may be configured such that the second illuminating source has at least one of a different wavelength, different polarity, and different intensity when the illumination from the second illuminating source arrives at the object as compared to the illumination from the illuminating source of the first optical channel.

Any of the imaging devices of the present disclosure may be configured such that the first optical channel further includes a second lens, where the second illumination pathway passes through the second lens and the illumination pathway of the illuminating source of the first optical channel does not pass through the second lens.

One or more embodiments of the present disclosure may include an imaging device that includes a first optical channel, the first optical channel including a first image sensor, a first optical imaging pathway from the first image sensor to cover a first zone of an object, a first illuminating source, the first illuminating source configured to be turned on or off, illumination from the first illuminating source following a first illumination path to the object, and a first set of lenses shared by both the first optical imaging pathway and the first illumination path. The imaging device may also include a second optical channel, the second optical channel including a second image sensor, a second optical imaging pathway from the second image sensor to cover a second zone of the object, the second zone at least partially overlapping the first zone, a second illuminating source, the second illuminating source configured to be turned on or off, illumination from the second illuminating source following a second illumination path to the object, and a second set of lenses shared by both the second optical imaging pathway and the second illumination path. The imaging device may further include a third optical channel, the third optical channel including a third image sensor, a third optical imaging pathway from the third image sensor to cover a third zone of the object, the third zone at least partially overlapping the first zone and the second zone, a third illuminating source, the third illuminating source configured to be turned on or off, illumination from the third illuminating source following a third illumination path to the object, and a third set of lenses shared by both the third optical imaging pathway and the third illumination path. The imaging device may also include a computing device configured to turn on at least one of the first illuminating source of the first optical channel and the second illuminating source of the second optical channel while capturing an image using the third image sensor of the third optical channel.

Any of the imaging devices of the present disclosure may be configured such that the first, the second, and the third optical channels are spaced and oriented equally about a convergence point.

Any of the imaging devices of the present disclosure may further include a hand-held casing within which the first, the second, and the third optical channels are contained.

Any of the imaging devices of the present disclosure may be configured such that the computing device is configured to turn on the first illuminating source of the first optical channel at a first wavelength and the second illuminating source of the second optical channel at a second wavelength while capturing an image using the third image sensor of the third optical channel.

BRIEF DESCRIPTION OF FIGURES

Example embodiments will be described and explained with additional specificity and detail through the use of the accompanying drawings in which.

DESCRIPTION OF EMBODIMENTS

The present disclosure relates to, inter alia, the use of a multi-channel imaging system to capture images of a subject using cross-channel illumination, where the different channels image overlapping regions of the subject. In particular, at least one of the channels include illumination capabilities in addition to image-capturing capabilities. Due to artifacts that may be created by illuminating in the same channel used to capture an image, images may be captured from channels that are not illuminating while the subject is illuminated from other channel(s) that are not currently capturing images. For example, when imaging a retina, cornea, or other curved surface, illuminating light that is coincident with an image being captured will be reflected back at the image capturing device to create blind spots, blurs, halos, etc. that distort the image and prevent useful image capturing. By illuminating from another channel, those artifacts may be avoided.

Figure 1A:
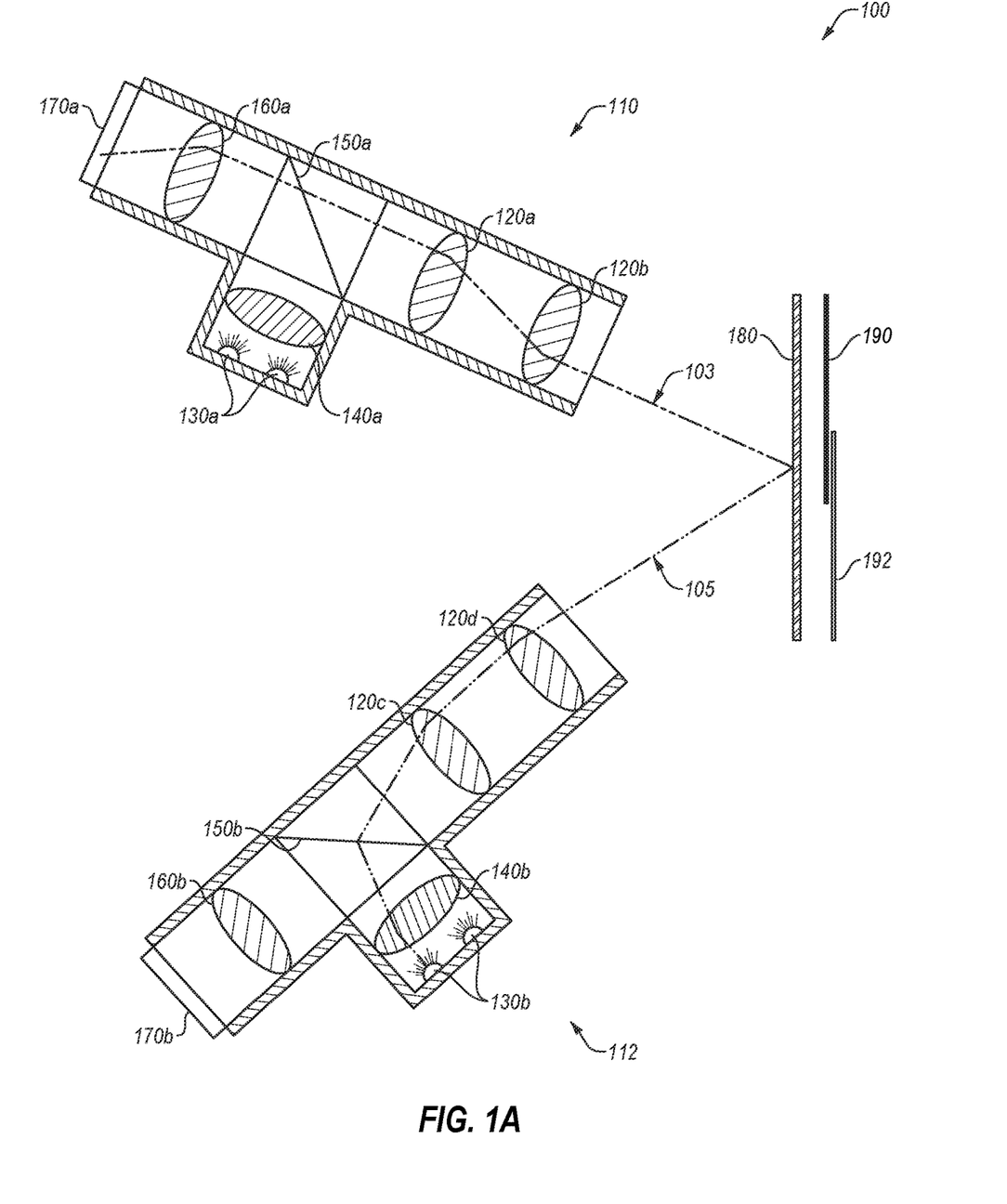
FIGS. 1A and 1B illustrate an example implementation of a multi-channel imaging system.
Figure 1B:
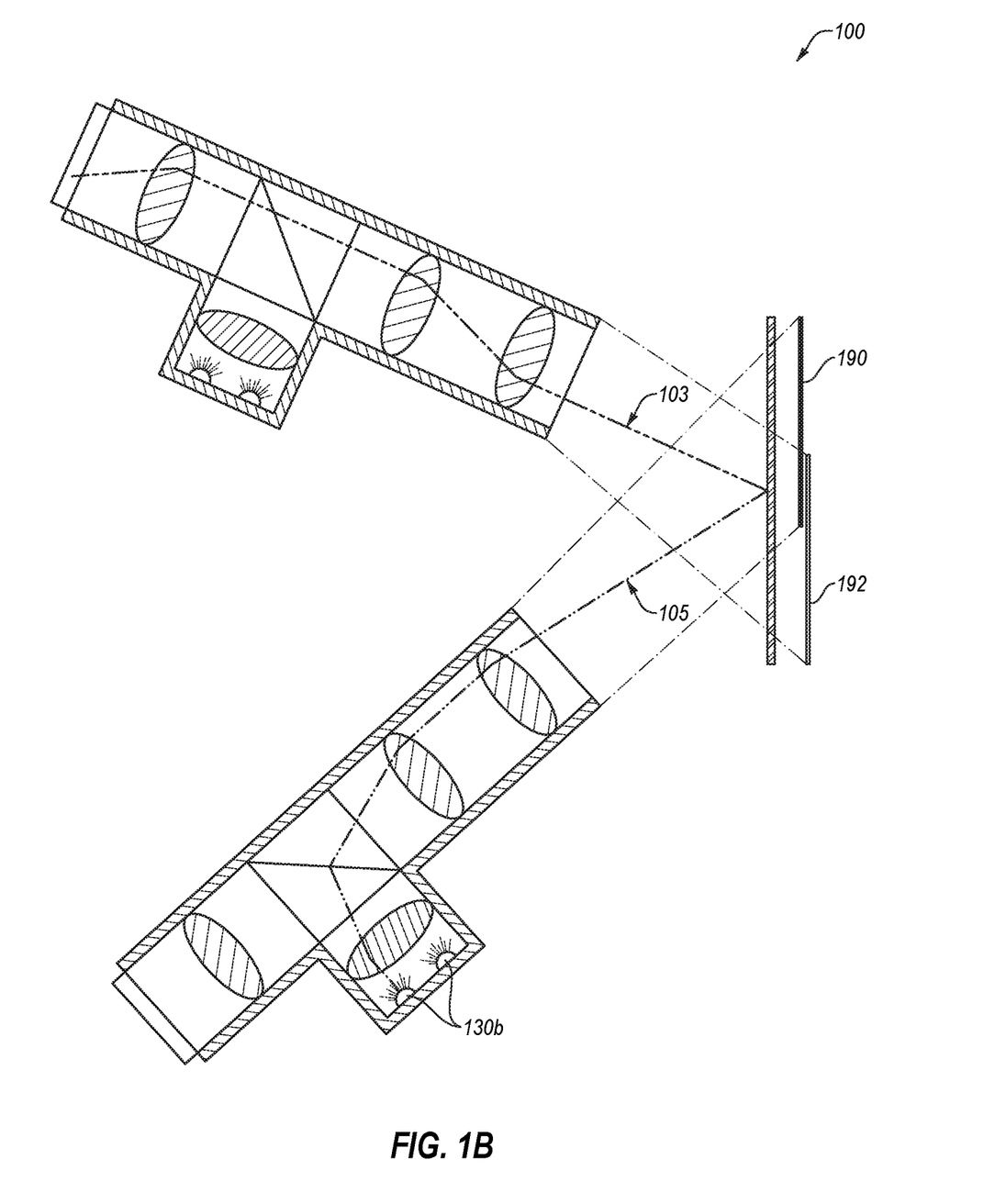

FIGS. 1A and 1B illustrate an example implementation of a multi-channel imaging system 100, in accordance with one or more embodiments of the present disclosure. The multi-channel imaging system 100 may include two similar optical channels, optical channel 110 and optical channel 112. Each of the optical channels may include shared optical lenses 120 (such as the optical lenses 120a-120d), illumination sources 130 (such as the illumination sources 130a-130b), illumination lenses 140 (such as the illumination lenses 140a-140b), a beam splitter 150 (such as the beam splitters 150a-150b), an imaging lens 160 (such as the imaging lens 160a-160b), and/or an image sensor 170 (such as the image sensors 170a-170b). The optical channels 110 and 112 may be configured to capture images of an object or scene 180. The optical channel 110 may capture images of and/or illuminate the zone 192 while the optical channel 112 may capture images of and/or illuminate zone 190.

Figure 4:
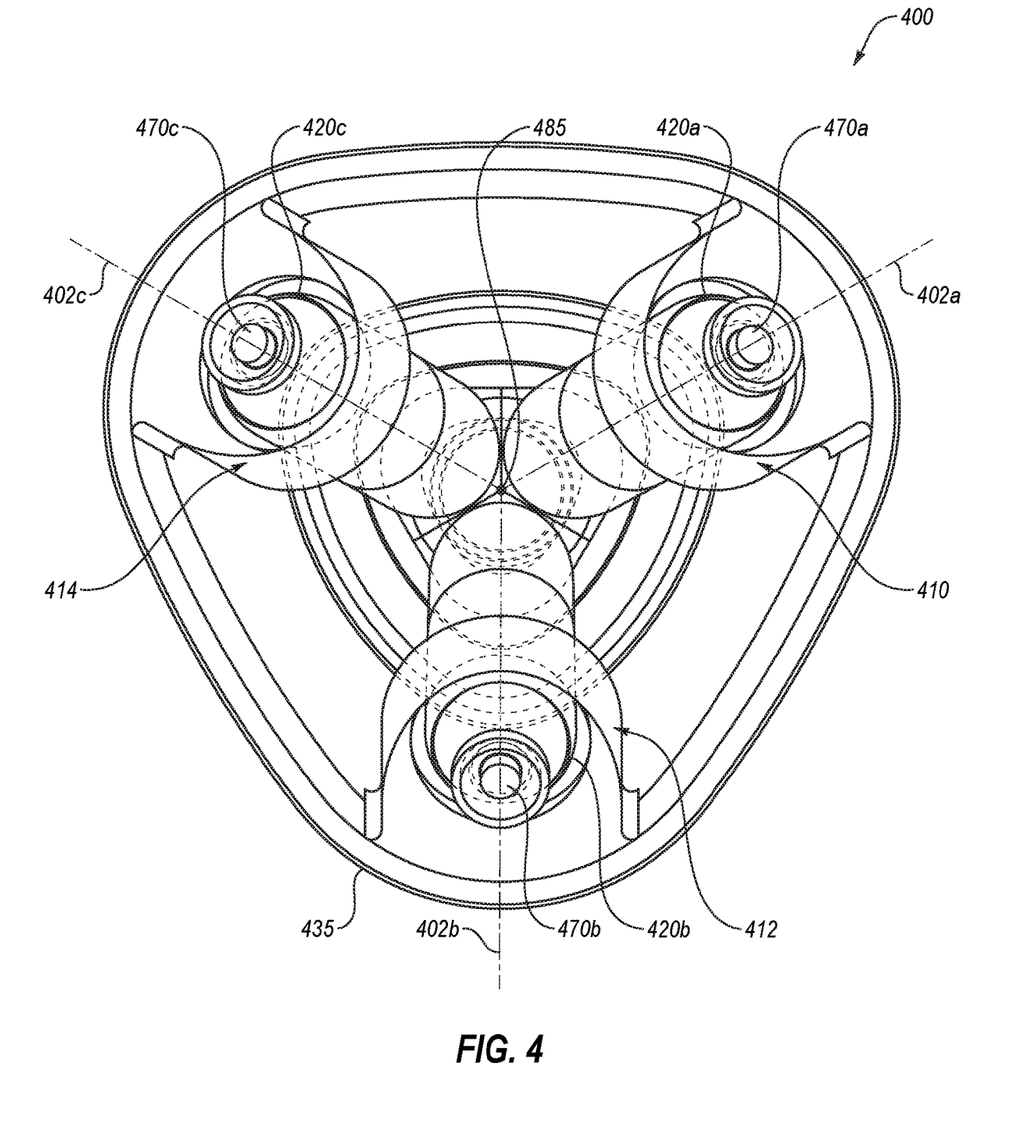
FIG. 4 illustrates another example multi-channel imaging system.

The optical channels 110 and 112 may be oriented in different directions to capture images/illuminate the object or scene 180. Stated another way, the optical channels 110 and 112 may be non-coplanar. An example of the different orientations is illustrated in FIGS. 1A and 1B, and another example is illustrated in FIG. 4. In some embodiments, the orientation may be such that the overlapping of the zone 190 and the zone 192 may be complete overlap or near complete overlap. In some embodiments, the orientation of the different imaging channels may be equidistant and/or equiangular about a convergence point that is within all of the overlapping regions. Additionally, while two optical channels 110 and 112 are illustrated in FIGS. 1A and 1B, it will be appreciated that any number of channels are contemplated, such as three (as illustrated in FIG. 4), four, five, six, eight, ten, or more, optical channels.

The beam splitter 150 may include any optical element configured to permit the passage and/or direction of light. In some embodiments, the beam splitter may include one or more prisms, mirrors, etc. In operation, the beam splitter 150 may be configured to direct the light from the illumination sources 130 towards the zone 190 and/or the zone 192. Additionally or alternatively, the beam splitter 150 may be configured to direct reflected/emitted light from the object or scene 180 towards the image sensor 170. While the term "light" may be used herein, it will be appreciated that the term is used for convenience in describing the travel, propagation, and/or use of electromagnetic (EM) waves and/or radiation, regardless of the wavelength of the EM waves. Thus, while the term "light" may be used, the EM waves may be of any wavelength such as ultraviolet, infrared, etc.

With respect to the components of the optical channels, the shared optical lenses 120, illumination lens 140, and imaging lens 160 may be any optical device configured to direct, refract, reflect, etc. light. The shared optical lenses 120 may be configured to facilitate both the guiding of light from the illumination sources 130 towards the object or scene 180 and the reception of light reflected/emitted from the object or scene 180 towards the image sensor 170 to be captured as an image. The illuminating lens 140 may be configured to direct light from the illumination sources 130 towards the object or scene 180. The imaging lens 160 may be configured to guide light reflected/emitted from the object or scene 180 towards the image sensor 170 to be captured as an image.

The illumination sources 130 may include any light emitting source, such as an array of light emitting diodes (LED), light bulbs, arc lamps, etc. In some embodiments, the illumination sources may be at different locations to illuminate different portions of the zone 190/zone 192. Additionally or alternatively, the illumination sources 130 may include light sources at different wavelengths/colors, and/or an ability for different intensities. In some embodiments, one or more of the illumination lens 140, beam splitter 150, and/or shared optical lenses 120 may be configured to diffuse the light from the illumination sources 130 such that the intensity of the light may be dissipated and applied over a broader region within the zone 190/zone 192.

The image sensor 170 may include any image capturing device, such as a charge-coupled device (CCD), a complimentary metal-oxide-semiconductor (CMOS), a back-side-illuminated CMOS (BSI-CMOS), etc. In these and other embodiments, the image sensor 170 may be coupled with a computing device (not shown) that may perform image processing on the image and/or combinations of multiple images, including multiple images from multiple image sensors (e.g., from the image sensor 170 from each of the optical channels 110 and 112).

In some embodiments, the illumination sources 130 may be in a branch of the optical pathways 110/112. For example, the optical channel 110 may include a branch off of the optical channel 110 with the beam splitter 150a at the intersection of the branch with the optical channel 110.

FIG. 1B illustrates an example of operation of the multi-channel imaging system 100. For example, as illustrated in FIG. 1B, the illumination sources 130b of the optical channel 112 may be activated such that the optical channel 112 illuminates the zone 190 of the object or scene 180 with the illumination 105. While the optical channel 112 is illuminating the zone 190, the optical channel 110 may receive the image light 103 to capture an image of the zone 192. As illustrated in FIG. 1B, due to the overlap in the zone 190 and zone 192, the illumination 105 illuminates a part of the zone 190 and the zone 192 such that an image captured of the zone 192 is at least partly illuminated. Furthermore, because the image light 103 is a reflection of the illumination 105 coming in at a different angle, rather than being illuminated by the illumination sources 130a-b in the optical channel 110, the image captured by the image sensor 170 avoids the artifacts in the image that would otherwise be present due to the coincident illumination light.

In some embodiments, the optical channels 110 and 112 may alternate between each other for illuminating and capturing images. For example, the optical channel 110 may capture in image of the object or scene 180 while the optical channel 112 illuminates the object or scene 180, followed by the optical channel 110 illuminating the object or scene 180 while the optical channel 112 captures an image of the object or scene 180. Using such an approach, multiple views of the object or scene 180 may be obtained where each view avoids the artifacts of illuminating from within the same optical channel. In some embodiments, such an approach may be used to generate a real-time video. For example, the images captured from the optical channel 110 and the optical channel 112 may be displayed in rapid succession as a video of the object or scene 180.

Modifications, additions, or omissions may be made to FIGS. 1A and 1B without departing from the scope of the present disclosure. For example, the multi-channel imaging system 100 may include more or fewer elements than illustrated in FIGS. 1A and 1B. For example, the multi-channel imaging system 100 may include any number of optical channels 110/112. As another example, any number of lenses, beam splitters, etc. may be used in the optical channels 110/112.

Figure 2:
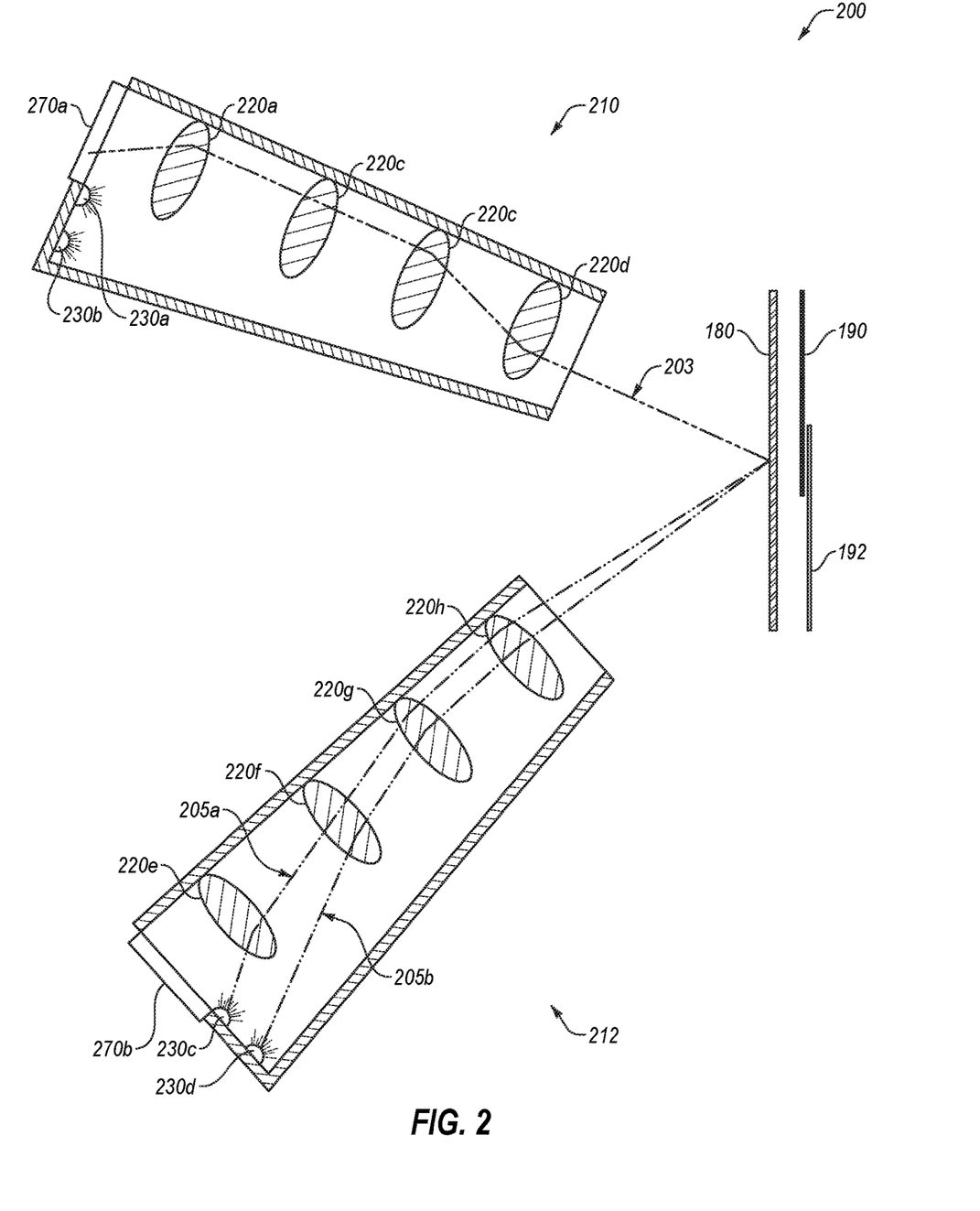
FIG. 2 illustrates another example implementation of a multi-channel imaging system.

FIG. 2 illustrates another example implementation of a multi-channel imaging system 200, in accordance with one or more embodiments of the present disclosure. As illustrated in FIG. 2, the multi-channel imaging system 200 may be positioned and/or configured to capture images of the object or scene 180 of FIGS. 1A and 1B, with the zone 190 and the zone 192 that overlap such that an optical channel 210 is configured to illuminate and/or capture images of the zone 192, and an optical channel 212 is configured to illuminate and/or capture images of the zone 190.

The multi-channel imaging system 200 may be similar or comparable to the multi-channel imaging system 100 of FIG. 1, with some variation. For example the first imaging channel 210 and the second imaging channel 212 may be similar or comparable to the first imaging channel 110 and the second imaging channel 112 of FIG. 1, the lenses 220 may be similar or comparable to the optical lenses 120 of FIG. 1, the illumination sources 230 may be similar or comparable to the illumination sources 130 of FIG. 1, and the image sensors 270 may be similar or comparable to the image sensors 170 of FIG. 1. With respect to some example variations from FIG. 2 compared to FIG. 1, rather than being displaced from the imaging path 103 in a different location and at an angle away from the sensor 170 as illustrated in FIG. 1, the illumination sources 230 may be laterally offset or coaxially offset from the image sensor 270 in FIG. 2. In some embodiments, the illumination sources 230 may be in the same enclosure as the image sensor 270. In these and other embodiments, a physical divider may be included between the illumination sources 230 and the image sensor 270. Because of the location of the illumination sources 230 relative to the image sensors 270, the optical channel 210 and/or the optical channel 212 may include multiple lenses 220 rather than a beam splitter.

As illustrated in FIG. 2, the optical channel 210 and the optical channel 212 may each include more than one illumination source 230. For example, the operation of the optical channels 210 and 212 with regard to illumination may be described with reference to the optical channel 212 as an example, but the description is equally applicable to the optical channel 210. Additionally, the operation of the optical channels 210 and 212 with regard to imaging may be described with reference to the optical channel 210 using the image sensor 270a as an example, but the description is equally applicable to the optical channel 212.

With regard to the illumination of the optical channel 212, in some embodiments, a first illumination source 232a may utilize a first lens 220e along a first illumination pathway 205a. The first illumination pathway 205a may then pass through one or more shared lenses 220f-h. A second illumination source 230b may be positioned, aligned, or otherwise configured such that when activated, the light from the illumination source 230b does not pass through the first lens 220e but may pass through one or more of the shared lenses 220f-h while traveling along a second illumination pathway 205b. In some embodiments, by using the different lenses and originating from different points, light emitted from the first illumination source 230a and the second illumination source 230b may arrive at approximately the same point in the zone 190. For example, as illustrated in FIG. 2, the first illumination pathway 205a and the second illumination pathway 205b converge at the object or scene 180. In other embodiments, the first illumination pathway 205a and the second illumination pathway 205b may illuminate different portions of the zone 190. In these and other embodiments, the different portions may overlap.

In some embodiments, the first and second illumination sources 230c and 230d may include light of different wavelengths, positions, polarities, intensity, etc. Additionally or alternatively, one or more of the properties of light emitted by the first and/or second illumination sources 230c and 230d may be modified based on which lenses the light passes through. In these and other embodiments, the various properties may be selectively modified based on which lenses are along the first illumination path 205a and which lenses are along the second illumination path 205b. For example, a lens along the first illumination path 205a and not used along the second illumination path 205b may diffuse the light such that light from the first illumination source 230c may be less intensely but more broadly spread across the zone 190, while the light from the second light source 230d may be focused on the zone 190 to provide a more narrow but more intense illumination of a portion of the object or scene 180.

With regard to imaging, the optical channel 210 may be configured to capture an image of the zone 192 while the optical channel 212 is illuminating the zone 190. In particular, as illustrated in FIG. 2, the imaging path 203 may correspond to the illumination channels 205a and/or 205b such that the overlapping portions of the zone 190 and the zone 192 may be illuminated and imaged, simultaneously, using different optical channels. Using such an approach, multiple illumination sources 230 (such as the illumination sources 230c and 230d) may be used to reduce the effect of shadows, to provide different wavelengths, etc.

In some embodiments such as those illustrated in FIG. 2, an optical channel may not include a beam splitter based on the location of the lenses and/or the location of the illumination sources and an image sensor. For example, by locating the illumination sources 230a and 230b at positions such that selective lenses are used, a beam splitter may be omitted. Additionally, while the illumination sources 230 are illustrated as being laterally offset from the image sensor 270 in one direction, the illumination sources 230 may be offset in multiple directions and/or axially from the image sensor 270. For example, the illumination source 230a may be offset in one direction relative to the image sensor 270a and the illumination source 230b may be offset in the opposite direction such that the image sensor 270a may include illumination sources on both sides of the image sensor 270a. Any number of illumination sources 230 may be positioned about the image sensor 270a.

Modifications, additions, or omissions may be made to FIG. 2 without departing from the scope of the present disclosure. For example, the multi-channel imaging system 200 may include more or fewer elements than illustrated in FIG. 2. For example, the multi-channel imaging system 200 may include any number of optical channels 210/212. As another example, any number of lenses, etc. may be used in the optical channels 210/212.

FIGS. 3A-3D illustrate various other example implementations of a multi-channel imaging system, in accordance with one or more embodiments of the present disclosure. The multi-channel imaging system of FIGS. 3A-3D may be similar or comparable to any multi-channel imaging systems of the present disclosure, such as those shown in FIGS. 1A-2. As illustrated in the views 300a, 300b, 300c, and 300d of FIGS. 3A-3D, respectively, an obstacle 315 or 318 may be located somewhere in the field between the optical channels and the object or scene. FIGS. 3A-3D serve to illustrate some example benefits of embodiments of the present disclosure in overcoming obstacles associated with imaging when an obstacle impedes imaging and/or illumination. Each of the views 300a-300d each include a respective imaging pathway 303a-303d and illumination pathway 305a-305d associated with a pair of optical channels 310 and 312.

The obstacle 315 may include any object, material, substance, etc. that may impede or otherwise prevent a clear line of sight from the imaging sensor and/or the illumination source to the object or scene 180. For example, the obstacle 315 may include a scratch on a lens or housing, a smudge or fingerprint on a lens, scar tissue in the eye, cataracts, clumps of vitreous gel (so-called "eye floaters"), etc.

Figure 3A:
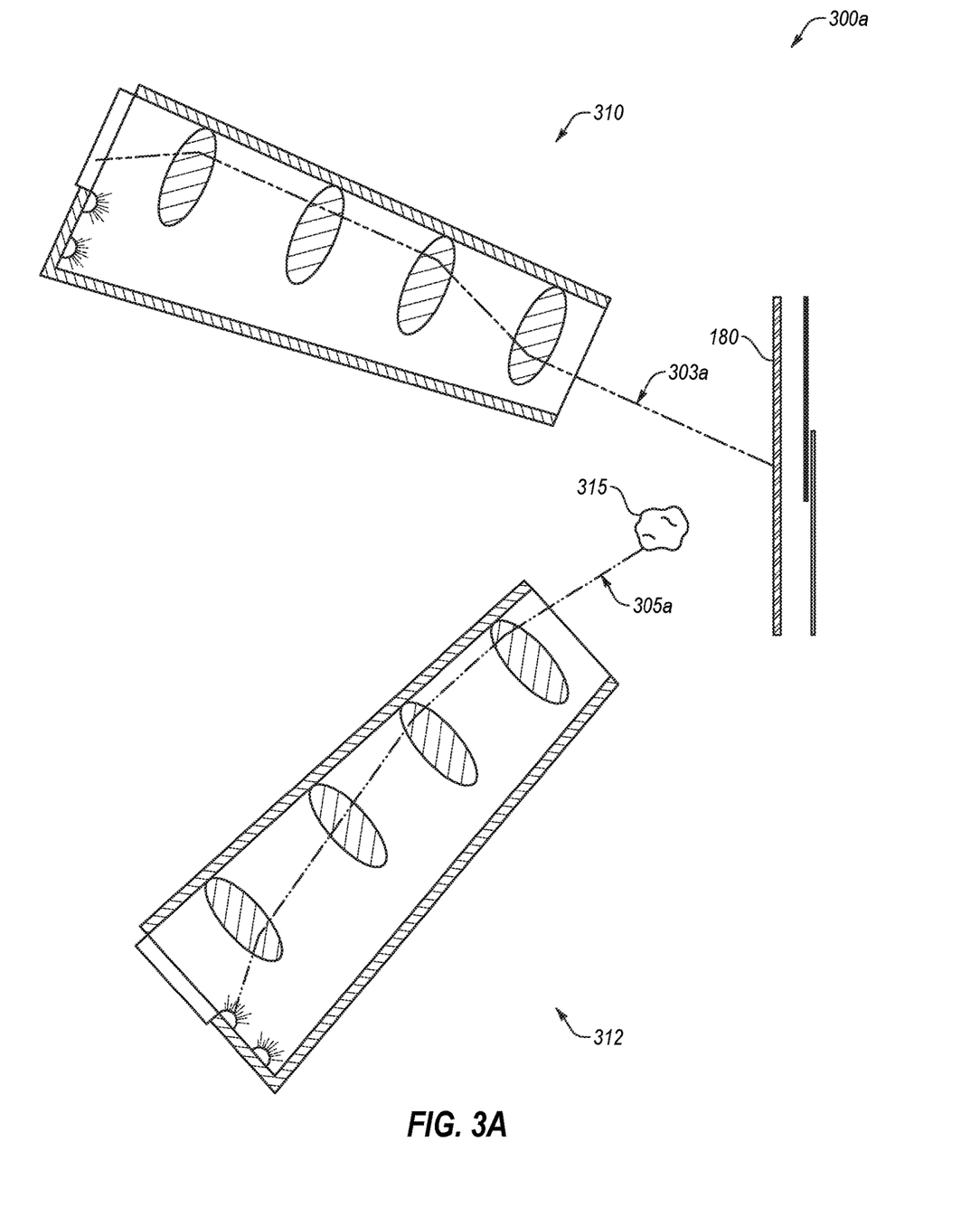
FIGS. 3A-3D illustrate various other example implementations of a multi-channel imaging system.
Figure 3B:
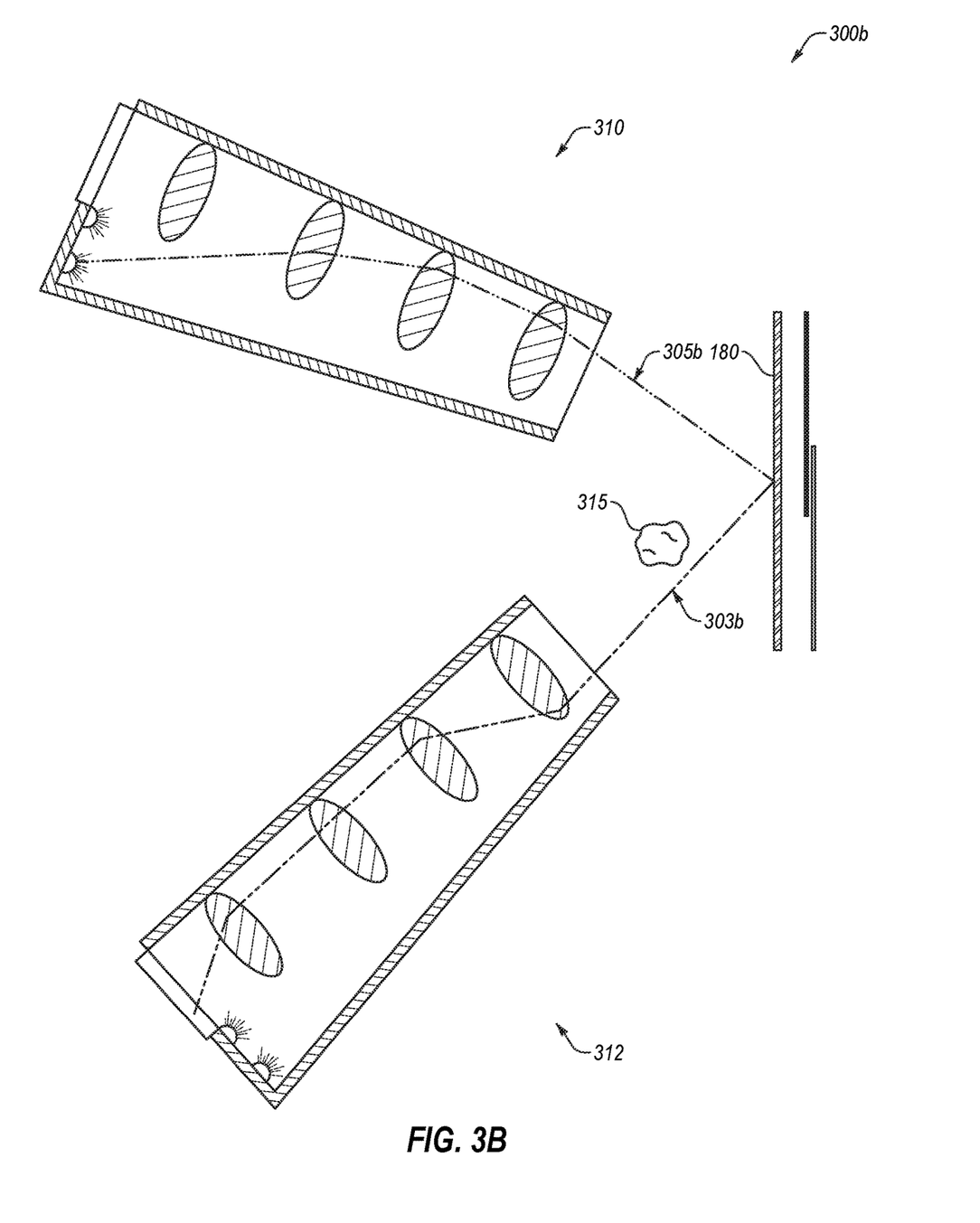
Figure 3C:
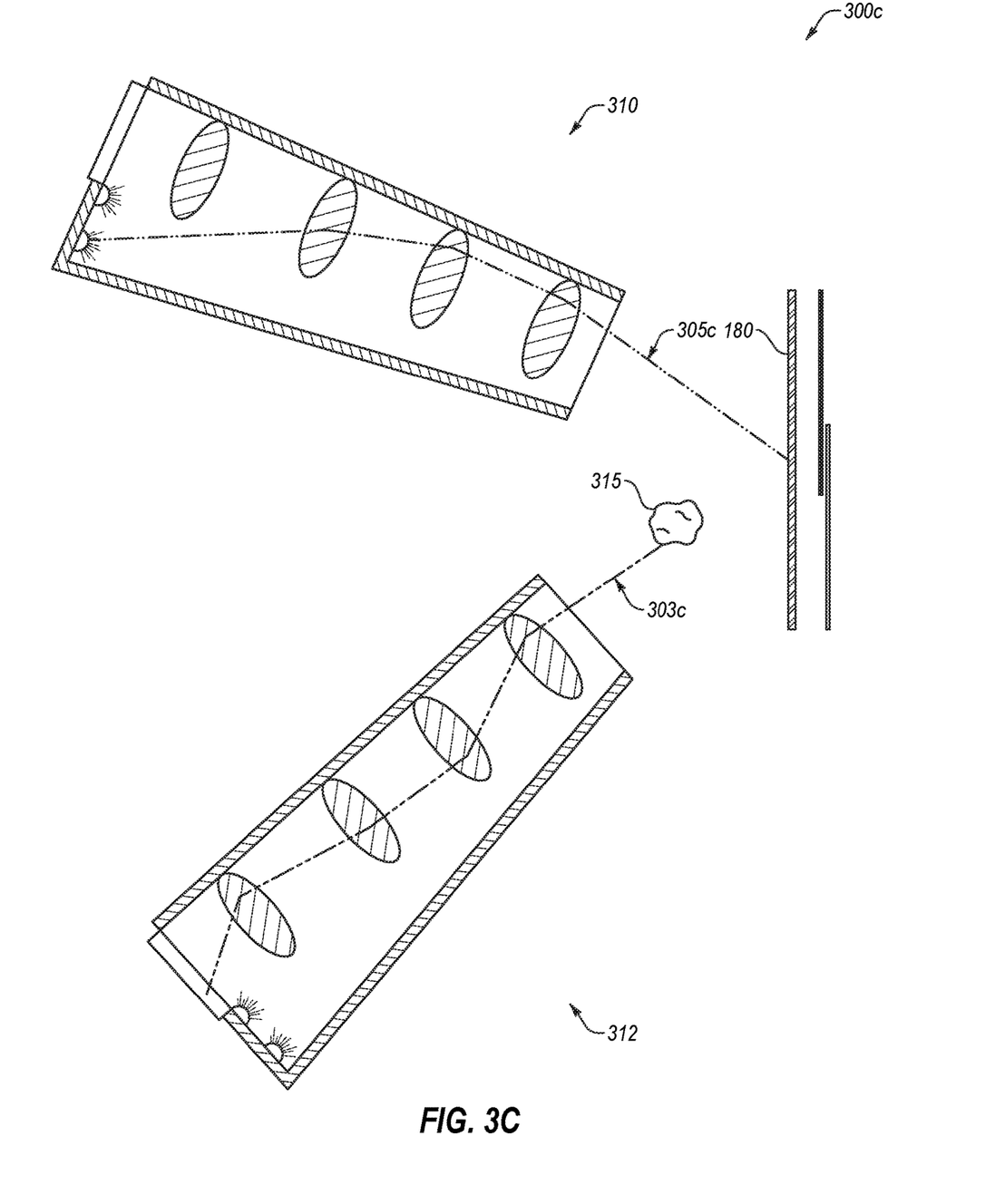

In the view 300a of FIG. 3A, the obstacle 315 may lie in the illumination pathway 305a such that a shadow may be cast on the object or scene 180 because of the obstacle 315. The view 300b of FIG. 3B illustrates a scenario in which the obstacle 315 may be outside of both the illumination pathway 305b and the imaging pathway 303b. In the view 300c of FIG. 3C, the obstacle 315 may lie in the imaging pathway 303c such that a clear view may be impeded, or the image that is captured may include an artifact or view of the obstacle 315 obstructing the view of at least part of the object scene 180.

In some embodiments, when multiple optical channels are used, such as the optical channels 310 and 312, images from the multiple optical channels may be used and stitched together to remove any artifacts created by the obstacle 315. For example, an image captured from the view 300a of FIG. 3A and the view 300b of FIG. 3B may be stitched together to remove the shadow cast by the obstacle 315 lying in the illumination pathway 305a but not in the imaging pathway 303b. In these and other embodiments, software may be used to detect missing regions of an image or imperfections in an image (e.g., the image captured from the view 300a or 300c), and to overlay, import, or otherwise insert the missing regions from overlapping views in other images (e.g., the image captured from the view 300b). In some embodiments, due to the different directions of the paths, the same optical channel may be obstructed in one view but not obstructed in another view. For example, when comparing the illumination pathway 305a of FIG. 3A with the imaging pathway 303b of FIG. 3B, it can be observed that the optical channel 312 has not moved relative to the obstacle 315, but the function of the optical channel 312 is not obstructed by the obstacle 315 in FIG. 3B while it is in FIG. 3A.

Figure 3D:
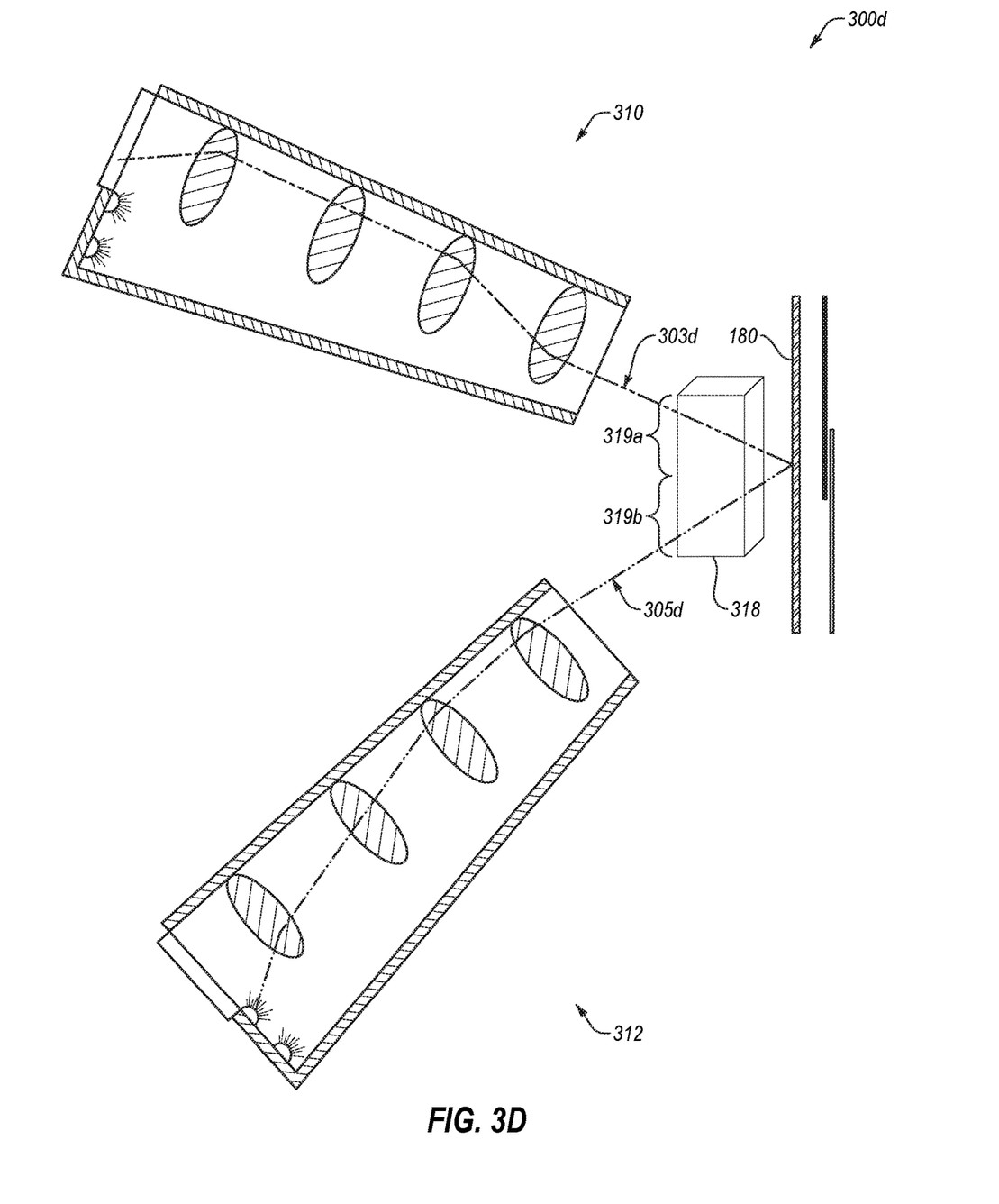

As illustrated in FIG. 3D, in some embodiments, the obstacle 318 may be located in the line of two or more optical channels simultaneously. For example, as illustrated in FIG. 3D, the obstacle 318 lies in the path of both optical channel 310 and optical channel 312. In these and other embodiments, the obstacle 318 may partially reflect or scatter light and/or imaging rays passing through the obstacle 318. Unwanted imaging artifacts in the optical channel 310, for example, may be reduced, accounted for, or otherwise removed or minimized if illumination from at least one of the optical channels 310 and 312 pass through a first region 319b of obstacle 318, while imaging rays belonging to optical channel 310 pass through a second region 319a of obstacle 318, where the first and second regions 319a and 319b of obstacle 318 are substantially non-overlapping.

In some embodiments, the obstacle 318 may reflect light into certain angles. For example the obstacle 318 may be a lens, a prism, or a window. Such a window may be flat or may include at least one curved surface. In these and other embodiments, unwanted imaging artifacts in the optical imaging channels may be suppressed, removed, etc. For example, an artifact while imaging via the optical channel 310 may be removed if the illumination of the illumination pathway 305d from the optical channel 312 passes through regions 319 of the obstacle 318 where the reflections are at a substantially different angle from the angle of imaging rays of the imaging pathway 303d belonging to the optical channel 310 that also pass through the obstacle 318. In some embodiments, the obstacle 318 may be the cornea or the crystalline lens of the patient's eye. Such embodiments may be pertinent for ophthalmic devices.

In some embodiments, the optical channels 310 and 312 may be configured to utilize imaging rays with preselected properties, such as preselected wavelengths or polarization states. For example, the image sensor may utilize one or more wavelength or polarization filters. In these and other embodiments, unwanted artifacts may be suppressed, minimized, or removed when illumination rays that are redirected by the obstacle 318 have a different, non-preferred property from the preferred property of the image sensor. In some embodiments, such an effect may be observed due to the obstacle 318 attenuating or otherwise mitigating the reflection, refraction, dissipation, etc. of illumination rays. For example, some illumination rays may utilize a first polarization state, and the obstacle 318 may specularly reflect such rays with only a small change in the polarization state, and the imaging path 303d of the optical channel 310 may be configured to utilize imaging signals in a second polarization state orthogonal to the first polarization state. In such an example, the illumination rays redirected by the obstacle 318 may be substantially attenuated when passing through the imaging path 303d of the optical channel 310, thereby diminishing imaging artifacts.

Modifications, additions, or omissions may be made to FIGS. 3A-3D without departing from the scope of the present disclosure. For example, the multi-channel imaging systems may include more or fewer elements than illustrated in FIGS. 3A-3D. As another example, the present disclosure may address and compensate for various types and numbers of obstacles in either the imaging or illumination pathways.

FIG. 4 illustrates another example multi-channel imaging system 400, in accordance with one or more embodiments of the present disclosure. The multi-channel imaging system 400 may include three optical channels 410, 412, and 414.

Each of the imaging paths 410, 412, and 414 may include an imaging sensor 470 (such as the imaging sensors 470a-c) and a lens 420 (such as the lenses 420a-c), as well as an illumination source (such as illustrated in FIGS. 1A, 1B, 2, and 3A-3D, but not shown in FIG. 4). Each of the optical channels may be configured to capture an image along a respective focal axis 402 (such as the focal axes 402a-c). The three focal axes 402a-c of the optical channels 410, 412, and 414 may converge on a convergence point 485, such as a point within the pupil if the retina is being imaged. Each of the optical channels 410, 412, and 414 may be contained within a hand-held housing 435 of a single device. In these and other embodiments, the functioning of the optical channels 410, 412, and/or 414 of the multi-channel imaging system 400 may be similar or comparable to that described with reference to FIGS. 1A-3D.

In some embodiments, the focal axes 402 may be equally positioned about a central axis pointing to the convergence point 485. For example, the focal axes 402 of the optical channels 410, 412, and 414 may be aimed at equal angles relative to each other, and all at equal angles relative to the central axis. In these and other embodiments, by utilizing such equal angles, the optical channels 410, 412, and 414 may be constructed in a similar manner such that during assembly and operation, the optical channels 410, 412, and 414 may be interchangeable.

Modifications, additions, or omissions may be made to FIG. 4 without departing from the scope of the present disclosure. For example, the multi-channel imaging system may include more or fewer elements than illustrated in FIG. 4. For example, the optical channels may include any number of lenses, illumination sources, etc. As another example, the optical channels may be symmetrical to each other or may be different with a different number and/or orientation of lenses and/or illumination sources. As an additional example, any number of optical channels may be included, such as six or eight.

Figure 5A:
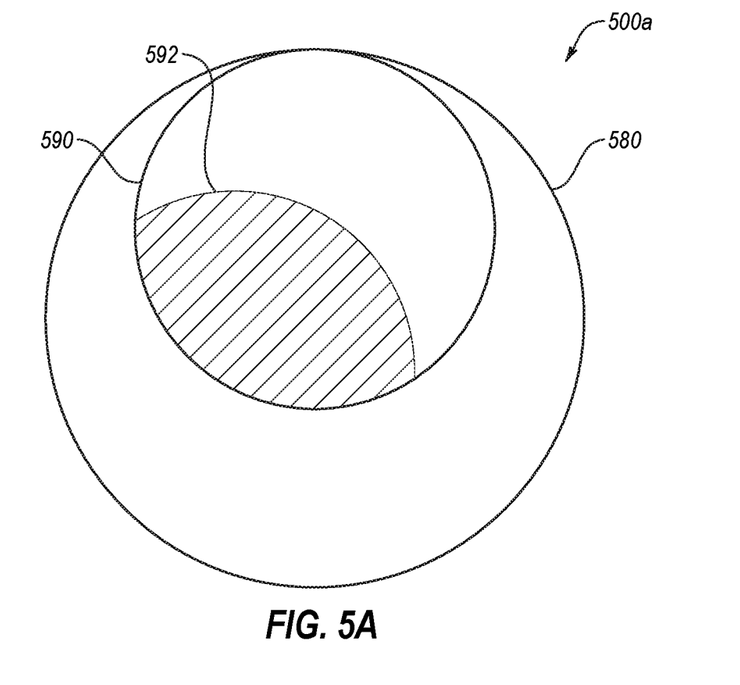
FIGS. 5A and 5B illustrate examples of cross-channel illumination in a multi-channel imaging system with three channels.
Figure 5B:
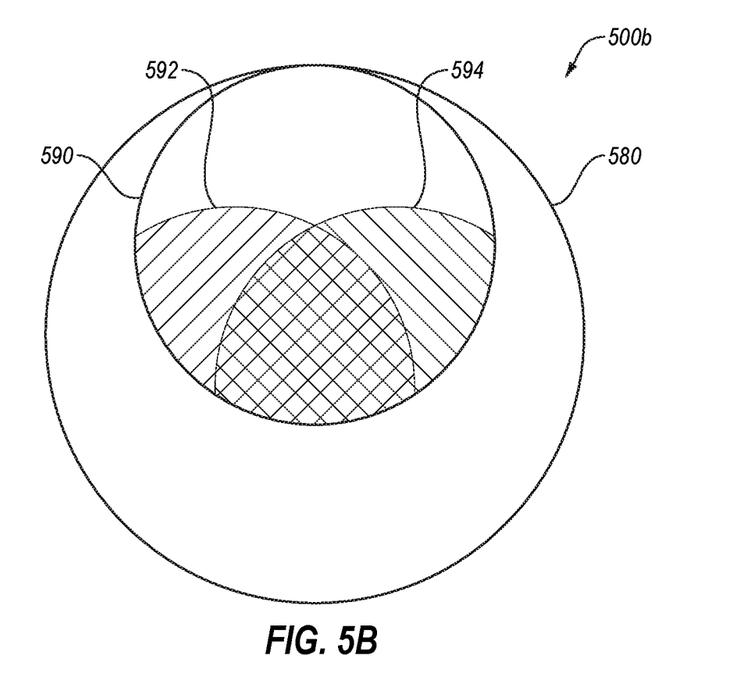

FIGS. 5A and 5B illustrate examples of cross-channel illumination 500a and 500b in a multi-channel imaging system with three channels, in accordance with one or more embodiments of the present disclosure. The cross-channel illumination 500a and 500b may be illuminated using any of the multi-channel imaging systems of the present disclosure, such as the multi-channel imaging system 400 of FIG. 4. FIG. 5A illustrates the cross-channel illumination 500a when a single channel is illuminating, and FIG. 5B illustrates the cross-channel illumination 500b when two channels are illuminating. FIGS. 5A and 5B are described with reference to the multi-channel imaging system 400 of FIG. 4 to illustrate an operating principle of some embodiments of the present disclosure.

FIGS. 5A and 5B illustrate an outermost circle representing the retina 580 as the object being imaged. The inner circle represents the zone 590 of the retina 580 imaged by the optical channel 412. The hash marked region 592 of FIG. 5A and the hash marked regions 592 and 594 of FIG. 5B illustrate the various portions of the zone 590 illuminated by the optical channels 410 and/or 414.

As illustrated in FIG. 5A, the optical channel 410 may illuminate a portion of the zone 590 imaged by the optical channel 412. In such a context, the optical channel 412 may capture an image of the retina 580 illuminated by an off-axis illumination source, such as illumination from the optical channel 410.

As illustrated in FIG. 5B, the optical channels 410 and 414 may both illuminate the retina 580 such that a greater portion of the zone 590 imaged by the optical channel 412 is illuminated. In such a context, the optical channel 412 may capture an image of the retina 580 illuminated by two off-axis illumination sources, such as illumination from the optical channels 410 and 414.

When more than one illumination source is used, such as illustrated in FIG. 5B, the illumination sources may emit light simultaneously or sequentially. Additionally or alternatively, the illumination sources may be positioned and/or configured to illuminate non-overlapping or overlapping zones of the object or scene to be imaged. In these and other embodiments, the different illumination sources may have different properties of light being emitted, such as different wavelengths, different intensities, different polarities, etc.

While two examples are provided, any number of options and iterations are possible and contemplated within the present disclosure. For example, the multi-channel imaging system 400 may capture a number of images in quick succession, for example illuminating with the optical channels 410 and 414 while capturing an image with the optical channel 412, illuminating with optical channels 410 and 412 while capturing an image with optical channel 414, and/or illuminating with optical channels 412 and 414 while capturing an image with optical channel 410. As another example, the multi-channel imaging system 400 may illuminate with the optical channel 410 while capturing images with the optical channels 412 and 414, illuminate with the optical channel 412 while capturing images with optical channels 410 and 414, and illuminate with optical channel 414 while capturing images with the optical channels 410 and 412.

In some embodiments, the different optical channels 410, 412, and/or 414 may include different illuminating options. For example, each optical channel may be equipped with multiple illuminating sources that are located such that when activated, they illuminate different portions of the object. For example, a first illuminating source of the optical channel 410 may be oriented to illuminate a large portion of the zone 590 imaged by the optical channel 412 and a second illuminating source of the optical channel 410 may be oriented to illuminate a large portion of the zone imaged by the optical channel 414 (not shown). As optical channel 412 is imaging, the first illuminating source may be activated and as optical channel 414 is imaging, the second illuminating source may be activated. In these and other embodiments, rather than using different illuminating sources located or oriented in different ways, one or more of the lenses and/or beam splitters may be moved between images to achieve the same effect. Additionally or alternatively, the illuminating sources and/or imaging sensors may be moved between images.

In some embodiments, the different optical channels may include illuminating sources of one or more various wavelengths. For example, each of the optical channels may be equipped with illuminating sources that illuminate at two different wavelengths. In these and other embodiments, imaging using differing wavelengths may be accomplished. For example, an illuminating source of the optical channel 410 may illuminate a portion of the zone imaged by the optical channel 412 at a first wavelength, and an illuminating source of the optical channel 414 may illuminate a portion of the zone 590 imaged by the optical channel 412 at a second wavelength. Such illumination may occur simultaneously (e.g., both wavelengths illuminating the same image) or in successive images (e.g., a first image illuminated by the first wavelength by the optical channel 410, and a second image illuminated by the second wavelength by the optical channel 414). As another example, an illuminating source of the optical channel 410 may illuminate a portion of the zone 590 imaged by the optical channel 412 at a first wavelength, an illuminating source of optical channel 414 may illuminate a portion of the zone 590 imaged by the optical channel 412 at a second wavelength, and an illuminating source of optical channel 412 may illuminate a portion of the zone 590 imaged by the optical channel 412 at a third wavelength.

In some embodiments, various images may be combined into a single image or into a video. For example, it is possible in rapid sequence to image with the optical channel 410 while illuminating with the optical channel 412 (or the optical channels 412 and 414), then image with the optical channel 412 while illuminating with the optical channel 414 (or the optical channels 410 and 414), then image with the optical channel 414 while illuminating with the optical channel 410 (or the optical channels 410 and 412), and then repeat the cycle. Using the continuing stream of images, a live video stream may be displayed that cycles between the three views (e.g., the view from the optical channels 410, 412, and 414). Additionally or alternatively, the video may be displayed at one third the frame rate of actual image capture with software stitching each sequence of three images from the three optical channels into a single uniformly (or more uniformly) illuminated image of the common imaging zone. In some embodiments, the software stitching or other software processing may be performed to bend, stretch, skew, or otherwise adjust the images from different perspectives such that each of the images are oriented and appear similar for the video. For example, because the optical channels 410 and 414 are from a different orientation than the optical channel 412, the same overlapped portion may be imaged but with certain portions stretched or skewed due to the focal axes 402 of the optical channels 410, 412, and 414. In these and other embodiments, each of the images may be stretched or skewed such that each of the overlapped regions of the images appear to have been taken from a common perspective. The stretching and/or skewing may or may not be uniform across an image. For example, the periphery of an image may be stretched or skewed more than the center portion of an image. Such stretching and/or skewing may be performed on any image, whether used in a video or not.

In some embodiments, the multi-channel imaging system as illustrated in FIGS. 1A, 1B, 2, 3A-3D, and/or 4 may include a computing device (not illustrated). Such a computing device may be configured to facilitate the performance of the operations described herein, such as capturing images, turning on or off illumination sources, image processing, video display, etc. Such a computing device may include a processor, a memory, etc. and may be in communication with and/or part of the multi-channel imaging system.

Generally, the processor may include any suitable special-purpose or general-purpose computer, computing entity, or processing device including various computer hardware or software modules and may be configured to execute instructions stored on any applicable computer-readable storage media. For example, the processor may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

It is understood that the processor may include any number of processors distributed across any number of networks or physical locations that are configured to perform individually or collectively any number of operations described herein. In some embodiments, the processor may interpret and/or execute program instructions and/or processing data stored in the memory. By interpreting and/or executing program instructions and/or process data stored in the memory, the device may perform operations, such as the operations performed by the retinal imaging device described in the present disclosure.

The memory may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor. By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. In these and other embodiments, the term "non-transitory" as used herein should be construed to exclude only those types of transitory media that were found to fall outside the scope of patentable subject matter in the Federal Circuit decision of *In re Nuijten,* 500 F.3d 1346 (Fed. Cir. 4007). In some embodiments, computer-executable instructions may include, for example, instructions and data configured to cause the processor to perform a certain operation or group of operations as described in the present disclosure.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method. For example, the dashed lines of the illumination paths and imaging paths are not meant to reflect an actual optical design, but are illustrative of the concepts of the present disclosure.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner. Additionally, the term "about" or "approximately" should be interpreted to mean a value within 10% of actual value.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. An imaging device, comprising:
a first and a second optical channel, each optical channel of the first and second optical channels including:
a discrete optical imaging pathway, the first and second optical channels aimed at different angles relative to each other, and each directed towards corresponding partially overlapping zones of an object;
an illuminating source, the illuminating source configured to be turned on or off, illumination from the illuminating source following an illumination path to the object;
one or more lenses shared by both the discrete optical imaging pathway and the illumination path; and
an image sensor; and
a computing device configured to alternate between
(i) turning off the illuminating source of the second optical channel, and turning on the illuminating source of the first optical channel so the illuminating source of the first optical channel is on while capturing a first image using the image sensor of the second optical channel, and
(ii) turning off the illuminating source of the first optical channel, and turning on the illuminating source of the second optical channel so the illuminating source of the second optical channel is on while capturing a second image using the image sensor of the first optical channel.

2. The imaging device of claim 1, wherein the first and the second optical channels are aimed at equal angles relative to a central axis between the first and the second optical channels, the central axis pointing towards the object.

3. The imaging device of claim 1, wherein the first and the second optical channels are aimed such that the discrete optical imaging pathways and the illumination paths of both the first and the second optical channels pass through a pupil of an eye to image a retina of the eye.

4. The imaging device of claim 1, wherein the first and the second images are combined to form a real time video of the object.

5. The imaging device of claim 4, wherein at least one of the first image and the second image are stretched or skewed such that the first image and the second image appear to have been captured from a common perspective.

6. The imaging device of claim 1, wherein a given region of the first image that includes an artifact is replaced with a corresponding region of the second image, the corresponding region of the second image showing the given region without the artifact.

7. The imaging device of claim 1, wherein the illuminating source is offset from the image sensor.

8. The imaging device of claim 7, wherein the illuminating source is offset axially from the image sensor within a same enclosure as the image sensor.

9. The imaging device of claim 7, wherein the first optical channel further comprises:
a beam splitter;
wherein the illuminating source is in a branch of the first optical channel, the beam splitter at an intersection of the branch of the first optical channel, the beam splitter directing illumination rays towards the object.

10. The imaging device of claim 1, wherein the first optical channel further includes a second illuminating source, the second illuminating source following a second illumination pathway and having different properties from the illuminating source of the first optical channel.

11. The imaging device of claim 10, wherein the second illuminating source has at least one of a different wavelength, different polarity, and different intensity when the illumination from the second illuminating source arrives at the object as compared to the illumination from the illuminating source of the first optical channel.

12. The imaging device of claim 10, the first optical channel further comprising a second lens, wherein the second illumination pathway passes through the second lens and the illumination path of the illuminating source of the first optical channel does not pass through the second lens.

13. An imaging device, comprising:
a first optical channel, the first optical channel including:
a first image sensor;
a first optical imaging pathway from the first image sensor to cover a first zone of an object;
a first illuminating source, the first illuminating source configured to be turned on or off, illumination from the first illuminating source following a first illumination path to the object; and
a first set of lenses shared by both the first optical imaging pathway and the first illumination path;
a second optical channel, the second optical channel including:
a second image sensor;
a second optical imaging pathway from the second image sensor to cover a second zone of the object, the second zone at least partially overlapping the first zone;
a second illuminating source, the second illuminating source configured to be turned on or off, illumination from the second illuminating source following a second illumination path to the object; and
a second set of lenses shared by both the second optical imaging pathway and the second illumination path;
a third optical channel, the third optical channel including:
a third image sensor;
a third optical imaging pathway from the third image sensor to cover a third zone of the object, the third zone at least partially overlapping the first zone and the second zone;
a third illuminating source, the third illuminating source configured to be turned on or off, illumination from the third illuminating source following a third illumination path to the object; and
a third set of lenses shared by both the third optical imaging pathway and the third illumination path; and
a computing device configured to turn on at least one of the first illuminating source of the first optical channel and the second illuminating source of the second optical channel while capturing an image using the third image sensor of the third optical channel.

14. The imaging device of claim 13, wherein the first, the second, and the third optical channels are spaced and oriented equally about a convergence point.

15. The imaging device of claim 13, further comprising a hand-held casing within which the first, the second, and the third optical channels are contained.

16. The imaging device of claim 13, wherein the computing device is configured to turn on the first illuminating source of the first optical channel at a first wavelength and the second illuminating source of the second optical channel at a second wavelength while capturing an image using the third image sensor of the third optical channel.

17. An imaging device, comprising:
- a first and a second optical channel, each optical channel of the first and second optical channels including:
  - a discrete optical imaging pathway, the first and second optical channels aimed at different angles relative to each other, and each directed towards corresponding partially overlapping zones of an object;
  - an illuminating source, the illuminating source configured to be turned on or off, illumination from the illuminating source following an illumination path to the object;
  - one or more lenses shared by both the discrete optical imaging pathway and the illumination path; and
  - an image sensor;
- a third optical channel, the third optical channel including:
  - a third image sensor;
  - a third optical imaging pathway from the third image sensor to the object; and
  - a third illuminating source configured to be turned on or off, illumination from the third illuminating source following a third illumination path to the object; and
- a computing device configured to turn on the illuminating source of the first optical channel while capturing an image using the image sensor of the second optical channel.

18. The imaging device of claim 17, wherein the computing device is configured to instruct the illuminating sources of the first and the second optical channels to be turned on while an image is captured using the third image sensor of the third optical channel.

19. The imaging device of claim 17, wherein the computing device is configured to instruct the third illuminating source to be turned on while images are captured by the image sensors of the first and the second optical channels.

* * * * *